US011883133B2

(12) United States Patent
Matsunaga et al.

(10) Patent No.: US 11,883,133 B2
(45) Date of Patent: Jan. 30, 2024

(54) INTERNAL BODY TEMPERATURE MEASUREMENT DEVICE AND INTERNAL BODY TEMPERATURE MEASUREMENT METHOD

(71) Applicant: Nippon Telegraph and Telephone Corporation, Tokyo (JP)

(72) Inventors: Daichi Matsunaga, Tokyo (JP); Yujiro Tanaka, Tokyo (JP); Michiko Seyama, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 590 days.

(21) Appl. No.: 17/252,821

(22) PCT Filed: Jun. 6, 2019

(86) PCT No.: PCT/JP2019/022568
§ 371 (c)(1),
(2) Date: Dec. 16, 2020

(87) PCT Pub. No.: WO2020/003960
PCT Pub. Date: Jan. 2, 2020

(65) Prior Publication Data
US 2021/0186337 A1    Jun. 24, 2021

(30) Foreign Application Priority Data

Jun. 27, 2018  (JP) .................................. 2018-121861

(51) Int. Cl.
*A61B 5/01* (2006.01)
(52) U.S. Cl.
CPC ........ *A61B 5/01* (2013.01); *A61B 2562/0271* (2013.01)

(58) Field of Classification Search
CPC .......... G01K 1/143; G01K 7/00; G01K 13/20; A61B 5/01; A61B 2562/0271
(Continued)

(56) References Cited

U.S. PATENT DOCUMENTS

2006/0056487 A1* 3/2006 Kuroda ................. G01K 1/165
                                                            374/E7.042
2015/0313474 A1* 11/2015 Goto .................... A61B 5/6833
                                                            600/549

FOREIGN PATENT DOCUMENTS

JP    2009222543 A    10/2009
JP    2013210326 A    10/2013
(Continued)

OTHER PUBLICATIONS

Nakagawa et al., "Wearable Core Temperature Thermometer Implemented by the MEMS Heat Flux Sensor," Journal of the Institute ofElectrical Engineers of Japan E, vol. 135, No. 8, 2015, pp. 343-348.
(Continued)

*Primary Examiner* — Mirellys Jagan
(74) *Attorney, Agent, or Firm* — Slater Matsil, LLP (57) ABSTRACT

An in-vivo temperature measurement device includes a plurality of thermal resistors, temperature sensors for measuring an epidermis temperature of a living body, and temperature sensors for measuring an upper surface temperature that are provided at both ends of the thermal resistors, respectively, a memory that stores an estimation model of the core temperature of the living body that takes into consideration a non-thermal equilibrium state of the living body, and thermal resistance values of the thermal resistors, and an arithmetic circuit that estimates, based on the plurality of temperatures measured by the temperature sensors and the temperature sensors, the core temperature of (Continued)

the living body using the estimation model and the thermal resistance values, and the thermal resistance values are different from one another.

10 Claims, 5 Drawing Sheets

(58) Field of Classification Search
USPC .......................................................... 374/110
See application file for complete search history.

(56) References Cited

FOREIGN PATENT DOCUMENTS

| WO | WO-2008068665 A1 | * | 6/2008 | ................ G01K 1/16 |
| WO | WO-2012042759 A1 | * | 4/2012 | ............. G01K 1/165 |
| WO | WO-2017108964 A1 | * | 6/2017 | ................ A61B 5/01 |
| WO | WO-2018152566 A1 | * | 8/2018 | ................ A61B 5/01 |

OTHER PUBLICATIONS

Nakayama et al., "Physiology of energy metabolism and thermo regulation," New Physiological Science System, 1987, pp. 96-97.

* cited by examiner

INTERNAL BODY TEMPERATURE MEASUREMENT DEVICE AND INTERNAL BODY TEMPERATURE MEASUREMENT METHOD

CROSS-REFERENCE TO RELATED APPLICATIONS

This application is a national phase entry of PCT Application No. PCT/JP2019/022568, filed on Jun. 6, 2019, which claims priority to Japanese Application No. 2018-121861, filed on Jun. 27, 2018, which applications are hereby incorporated herein by reference.

TECHNICAL FIELD

The present invention relates to an in-vivo temperature measurement device and an in-vivo temperature measurement method for measuring a core temperature of a living body.

BACKGROUND

In recent years, social jet-lag has been a problem. This is a problem that causes various physical and mental disorders due to the disagreement between the social time and the circadian time or the circadian system of each person who live a life and leads to lifestyle-related diseases. The circadian time can be known from various endocrine substances or vital information. The endocrine substances require several hours for measurement and cause both mental and physical loads.

In a living body, a temperature region not being affected by a change in outside-air temperature exists in a part located beyond a certain depth between the epidermis and a core (hereinafter, the temperature of such a part being referred to as "core temperature"). It is known that measurement of changes in core temperature as vital information is useful for grasping the circadian system.

The temperature of the core is measured by a method of inserting a probe of a thermometer into the body or swallowing the thermometer, but it can be said that such a method is not good in terms of hygiene and causes a large physical and mental burden. Therefore, a non-invasive method from outside of the body is required for measurement, and it can be said that a percutaneous temperature measurement method is particularly useful for easy and daily body temperature management (for example, see Non-Patent Literature 2).

Conventionally, a percutaneous thermometer has been used to measure the body temperature under the armpit or in the oral cavity, but it cannot be always said to reflect the core temperature for the following reasons. The reason is that it takes a time for the temperature to be transmitted from the core to the skin because thermal capacity and thermal resistance of the subcutaneous tissue change due to the amount of a blood flowing in the capillaries. Further, since the percutaneously measured temperatures are different from each other, the core temperature may not be reflected.

Therefore, there has been proposed a method of correcting the core temperature taking into consideration the time taken for the temperature to be transmitted from the core to the skin. However, a formula is established in such a method assuming that the temperature is in a sufficiently stable thermal equilibrium state, resulting in a cause of error in measuring the core temperature which changes every moment. Since the outside-air temperature, the deep body temperature, and the thermal resistance of the subcutaneous tissue change with time, it can be said that the living body is always in a non-thermal equilibrium state. Therefore, accuracy may be insufficient in the estimation of the core temperature using the conventional estimation model.

Citation List

Non-Patent Literature

Non-Patent Literature 1: Akio Nakayama, "New Physiology System Volume 22", Igaku-Shoin Ltd. (1987)

Non-Patent Literature 2: Shinya Nakagawa et al., "Wearable Core Temperature Thermometer implemented by the MEMS Heat Flux Sensor", Transactions E of The Institute of Electrical Engineers of Japan, Volume 135 (2015), No. 8, p. 343-348.

SUMMARY

Technical Problem

Embodiments of the present invention have been made to solve the above-described problems, and an object thereof is to provide an in-vivo temperature measurement device capable of more accurately estimating a core temperature that changes every moment.

Means for Solving the Problem

In order to solve the above-described problems, an in-vivo temperature measurement device according to embodiments of the present invention includes: a plurality of thermal resistors; first temperature sensors and second temperature sensors provided at both ends of the thermal resistors, respectively; a storage unit that stores an estimation model of a core temperature of a living body that takes into consideration a non-thermal equilibrium state of the living body, and thermal resistance values of the thermal resistors; and an arithmetic circuit that, based on a plurality of temperatures measured by the first temperature sensors and the second temperature sensors, estimates the core temperature of the living body using the estimation model and the thermal resistance values of the thermal resistors, wherein the first temperature sensors are provided on the thermal resistors to be closer to the living body and measures a first temperature indicating an epidermis temperature of the living body, the second temperature sensors are provided on the thermal resistors to be opposite to the living body and measure a second temperature at a position away from the living body, and the thermal resistance values of the plurality of thermal resistors are different from one another.

In the in-vivo temperature measurement device according to embodiments of the present invention, the arithmetic circuit may include: a time count unit that counts measurement times at which the first temperature sensors and the second temperature sensors measure the plurality of temperatures; and an estimation unit that, based on the plurality of temperatures measured by the first temperature sensors and the second temperature sensors at the measurement times, estimates the core temperature of the living body using the estimation model and the thermal resistance values of the thermal resistors, and the arithmetic circuit may generate time-series data in which the measurement time and the core temperature estimated by the estimation unit are associated with each other.

In the in-vivo temperature measurement device according to embodiments of the present invention, the number of the plurality of thermal resistors may be at least three.

In the in-vivo temperature measurement device according to embodiments of the present invention, the estimation model may be represented by a following expression:

Formula 1

$$T_C = \frac{T_1(T'_{S2}T_{S3} - T'_{S3}T_{S2}) + \frac{R_{S1}}{R_{S2}}T_2(T'_{S3}T_{S1} - T'_{S1}T_{S3}) + \frac{R_{S1}}{R_{S3}}T_3(T'_{S1}T_{S2} - T'_{S2}T_{S1})}{T_1(T'_{S2} - T'_{S3}) + \frac{R_{S1}}{R_{S2}}T_2(T'_{S3} - T'_{S1}) + \frac{R_{S1}}{R_{S3}}T_3(T'_{S1} - T'_{S2})}$$

wherein, TC indicates the core temperature at the measurement time t, RSi (i=1, 2, 3) indicates the thermal resistance values of the thermal resistors, TSi indicates the first temperatures measured by the first temperature sensors, Ti=(TSi(t)−TUi(t)), (TUi indicates the second temperatures measured by the second temperature sensors), and TSi'=dTSi(t)/dt.

An in-vivo temperature measurement method according to embodiments of the present invention includes: a temperature measurement step of measuring a plurality of temperatures with first temperature sensors and second temperature sensors provided at both ends of a plurality of thermal resistors, respectively; and an arithmetic step of estimating, using an estimation model of a core temperature that takes into consideration a non-thermal equilibrium state of a living body stored in a storage unit, and thermal resistance values of the thermal resistors, the core temperature of the living body based on the plurality of temperatures measured in the temperature measurement step, wherein the first temperature sensors are provided on the thermal resistors to be closer to the living body and measures a first temperature indicating an epidermis temperature of the living body, the second temperature sensors are provided on the thermal resistors to be opposite to the living body and measure a second temperature at a position away from the living body, and the thermal resistance values of the plurality of thermal resistors are different from one another.

Effects of Embodiments of the Invention

According to embodiments of the present invention, based on a plurality of temperatures measured by a plurality of temperature sensors provided at both ends of a plurality of thermal resistors, respectively, a core temperature of a living body is estimated using an estimation model of the core temperature that takes into consideration a non-thermal equilibrium state in the living body. Accordingly, it is possible to more accurately estimate the core temperature that changes every moment.

DETAILED DESCRIPTION OF ILLUSTRATIVE EMBODIMENTS

A preferred embodiment of the present invention will be described in detail below with reference to FIGS. 1 to 9B.

Principle of Embodiments of Invention

First, a principle of the an in-vivo temperature measurement device according to embodiments of the present invention will be described with reference to FIGS. 1 to 5.

Figure 1:
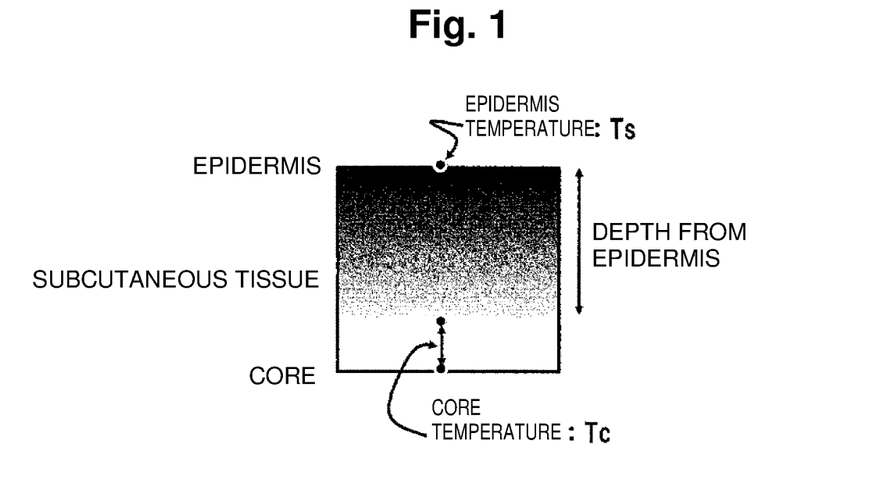
FIG. 1 is a diagram schematically illustrating a temperature distribution of subcutaneous tissue of a living body.

FIG. 1 is a diagram schematically illustrating a temperature distribution of subcutaneous tissue of a living body. As shown in FIG. 1, a region of a core temperature exists in a part of the living body located beyond a certain depth in a depth direction from the epidermis to the subcutaneous tissue, the core temperature not being affected by a change in outside-air temperature. A temperature in such a region is measured as a core temperature $T_C$. Usually, an epidermis temperature $T_S$ is lower than the core temperature $T_C$, and a temperature gradient occurs from the core to the epidermis.

Figure 2:
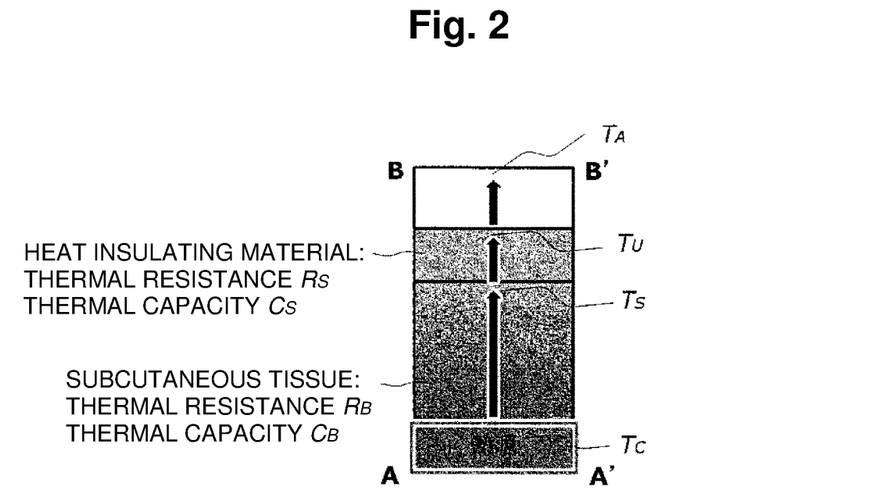
FIG. 2 is a diagram showing a thermal model of human body for explaining a principle of embodiments of the present invention.

FIG. 2 is a diagram showing a thermal model of human body (AA'B'B). The thermal model of human body includes a region from the region where the core of the living body is located to the outside air. Specifically, the thermal model of human body shown in FIG. 2 indicates the core where a heat source of the living body exists, the subcutaneous tissue of the living body, a heat insulating material (thermal resistor) existing in contact with the outside of the living body, a temperature at each part up to the outside air of the heat insulating material, a thermal resistance, and a thermal capacity.

A temperature in the core region of the living body, in which the heat source exists, is represented by the core temperature $T_C$. A temperature passing through the subcutaneous tissue from the heat source is represented by the epidermis temperature $T_S$. The subcutaneous tissue includes a thermal resistance $R_B$ and a thermal capacity $C_B$. Further, a temperature passing through the heat insulating material provided outside in contact with the epidermis of the living body is represented by an upper surface temperature $T_U$. The heat insulating material includes the thermal resistance $R_S$ and the thermal capacity $C_S$. In addition, a temperature in air is represented by an air temperature $T_A$.

Figure 3:
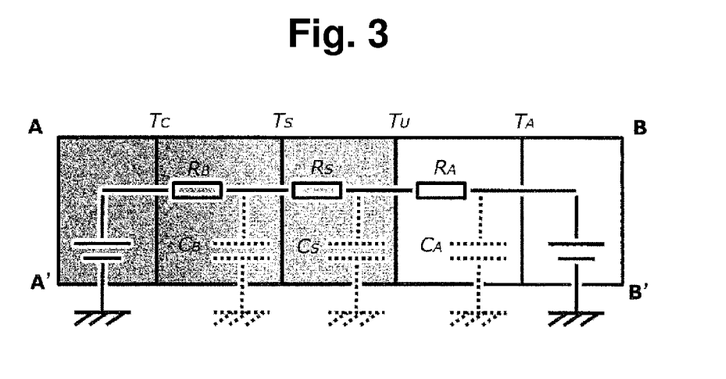
FIG. 3 is a diagram showing an equivalent circuit of FIG. 2.

FIG. 3 is an equivalent circuit in which the thermal model of human body shown in FIG. 2 is depicted as an RC series circuit. As shown in FIG. 3, in a technique for measuring the core temperature $T_C$ of a conventional example, the core temperature $T_C$ is derived from the epidermis temperature $T_S$ and the upper surface temperature $T_U$ when respective capacitors in the equivalent circuit are fully charged and enter a steady state (for example, see Non-Patent Literature 2). From the thermal resistance $R_B$ of the subcutaneous tissue, the thermal resistance $R_S$ of the heat insulating material (thermal resistor), the epidermis temperature $T_S$, and the upper surface temperature $T_U$, the core temperature $T_C$ can be calculated using Expression (1) below.

Formula 2

$$T_C = T_S + \frac{R_B}{R_S}(T_S - T_U) \quad (1)$$

Using two thermal resistance values, for example, a thermal resistance value $R_{S1}$ of a first thermal resistor and a thermal resistance value $R_{S2}$ of a second thermal resistor as known thermal resistance $R_S$ of the heat insulating material in Expression (1) described above, two expressions are created to cancel out the unknown thermal resistance $R_B$ of the subcutaneous tissue. However, as described above, the thermal resistance $R_B$ of the subcutaneous tissue, the thermal resistance $R_S$ of the heat insulating material, the epidermis temperature $T_S$, the upper surface temperature $T_U$, and the core temperature $T_C$ are actually not in a steady state. Therefore, it is considered that each of the values changes with time, and a new estimation model is constructed.

Figure 4:
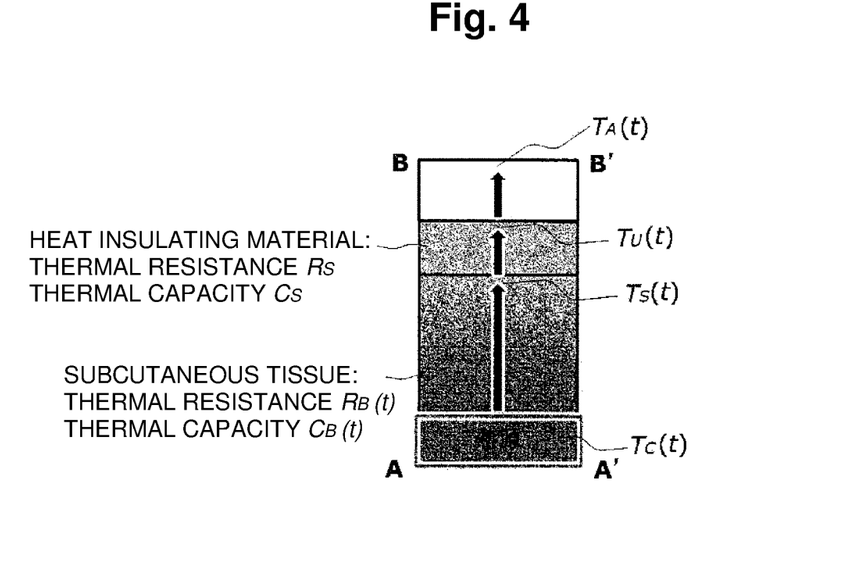
FIG. 4 is a diagram showing a thermal model of human body for explaining a principle of embodiments of the present invention.
Figure 5:
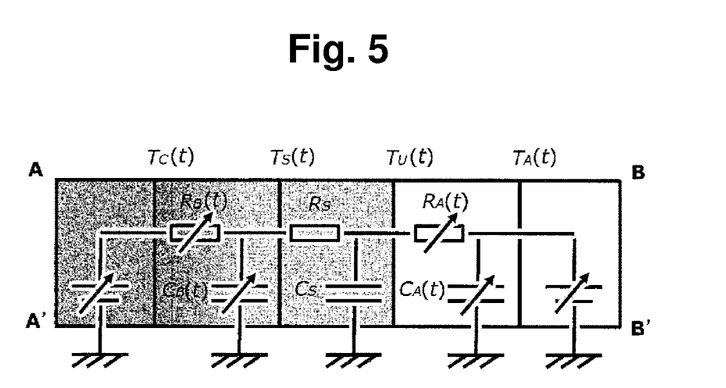
FIG. 5 is a diagram showing an equivalent circuit of FIG. 4.

FIGS. 4 and 5 are diagrams showing a newly constructed thermal model of human body and an equivalent circuit thereof.

As shown in FIGS. 4 and 5, a voltage $V_{CB}(t)$ applied to a thermal capacity $C_B(t)$ of the subcutaneous tissue is expressed by Expression (2) below. Further, Expression (2) is modified to derive Expression (3) indicating a core temperature $T_C(t)$.

Formula 3

$$V_{CB}(t) = C_B(t)\frac{dT_S(t)}{dt} = \frac{T_C(t) - T_S(t)}{R_B(t)} - \frac{T_S(t) - T_U(t)}{R_S} \quad (2)$$

$$\Leftrightarrow T_C(t) = T_S(t) + \frac{R_B(t)}{R_S}(T_S(t) - T_U(t)) + C_B R_B(t)\frac{dT_S(t)}{dt} \quad (3)$$

Using three thermal resistance values different from one another, for example, a thermal resistance value $R_{S1}$ of a first thermal resistor, a thermal resistance value $R_{S2}$ of a second thermal resistor, and a thermal resistance value $R_{S3}$ of a third thermal resistor as known thermal resistance $R_S$ of the heat insulating material in Expression (3) described above, three expressions are created to cancel out the unknown thermal resistance $R_B(t)$ of the subcutaneous tissue and the thermal capacity $C_B(t)$ of the subcutaneous tissue.

More specifically, using Expression (3) described above, a determinant indicated by Expression (4) below is created using an epidermis temperature $T_{S1}(t)$ and an upper surface temperature $T_{U1}(t)$ in the first thermal resistor ($R_{S1}$), an epidermis temperature $T_{S2}(t)$ and an upper surface temperature $T_{U2}(t)$ in the second thermal resistor ($R_{S2}$), and an epidermis temperature $T_{S3}(t)$ and an upper surface temperature $T_{U3}(t)$ in the third thermal resistor ($R_{S3}$).

Formula 4

$$\begin{cases} T_C(t) = T_{S1}(t) + \frac{R_B(t)}{R_{S1}}(T_{S1}(t) - T_{U1}(t)) + C_B R_B(t)\frac{dT_{S1}(t)}{dt} \\ T_C(t) = T_{S2}(t) + \frac{R_B(t)}{R_{S2}}(T_{S2}(t) - T_{U2}(t)) + C_B R_B(t)\frac{dT_{S2}(t)}{dt} \\ T_C(t) = T_{S3}(t) + \frac{R_B(t)}{T_{S3}}(T_{S3}(t) - T_{U3}(t)) + C_B R_B(t)\frac{dT_{S3}(t)}{dt} \end{cases} \quad (4)$$

$$\Leftrightarrow \begin{pmatrix} 1 - \frac{T_{S1}(t)-T_{U1}(t)}{R_{S1}} & -\frac{dT_{S1}(t)}{dt} \\ 1 - \frac{T_{S2}(t)-T_{U2}(t)}{R_{S2}} & -\frac{dT_{S2}(t)}{dt} \\ 1 - \frac{T_{S3}(t)-T_{U3}(t)}{R_{S3}} & -\frac{dT_{S3}(t)}{dt} \end{pmatrix} \begin{pmatrix} T_C(t) \\ R_B(t) \\ C_B R_B(t) \end{pmatrix} = \begin{pmatrix} T_{S1}(t) \\ T_{S2}(t) \\ T_{S3}(t) \end{pmatrix}$$

Solving Expression (4) described above, the core temperature $T_C(t)$ is expressed by Expression (5) below. Here, Expression (5) satisfies following conditions: $T_i = (T_{Si}(t) - T_{Ui}(t))$, $T_{Si}' = dT_{Si}(t)/dt$, ($i = 1, 2, 3$).

Formula 5

$$T_C = \frac{T_1(T_{S2}'T_{S3} - T_{S3}'T_{S2}) + \frac{R_{S1}}{R_{S2}}T_2(T_{S3}'T_{S1} - T_{S1}'T_{S3}) + \frac{R_{S1}}{R_{S3}}T_3(T_{S1}'T_{S2} - T_{S2}'T_{S1})}{T_1(T_{S2}' - T_{S3}') + \frac{R_{S1}}{R_{S2}}T_2(T_{S3}' - T_{S1}') + \frac{R_{S1}}{R_{S3}}T_3(T_{S1}' - T_{S2}')} \quad (5)$$

As described above, the in-vivo temperature measurement device according to embodiments of the present invention is configured to measure the epidermis temperatures $T_{S1}$ to $T_{S3}$ and the upper surface temperatures $T_{U1}$ to $T_{U3}$ measured by the thermal resistors (thermal resistance values $R_{S1}$ to $R_{S3}$) and to obtain an estimation value of the core temperature $T_C$ by applying the measured temperatures to Expression (5) which is the newly constructed estimation model of the core temperature $T_C$.

Embodiment

An in-vivo temperature measurement device 1 according to embodiments of the present invention will be described in detail below.

Figure 7:
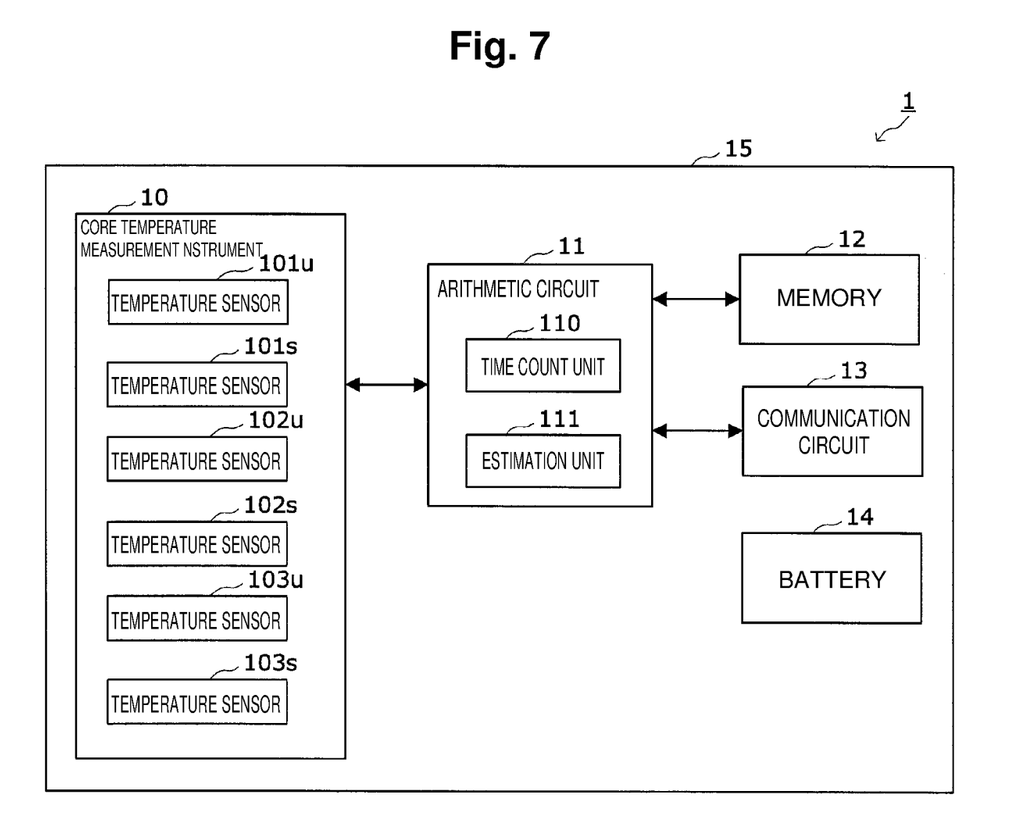
FIG. 7 is a block diagram showing the configuration of the in-vivo temperature measurement device according to the embodiment of the present invention.
Figure 8:
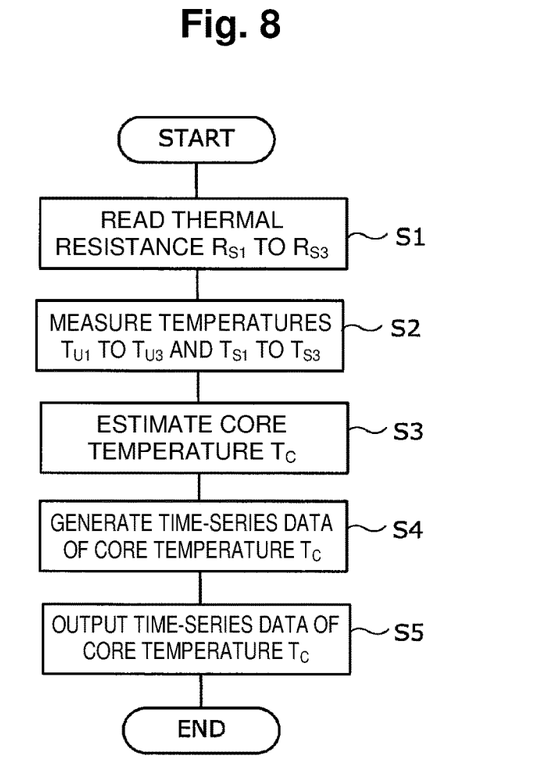
FIG. 8 is a flowchart for explaining an operation of the in-vivo temperature measurement device according to the embodiment of the present invention.

FIGS. 7 and 8 are block diagrams showing a configuration of the in-vivo temperature measurement device 1 according to the present embodiment. The in-vivo temperature measurement device 1 includes, on a sheet-shaped base 15, a core temperature measurement instrument 10, an arithmetic circuit 11, a memory 12, a communication circuit 13 functioning as an I/F circuit with the outside, and a battery 14 for supplying power to the arithmetic circuit 11 and the communication circuit 13.

Figure 6:
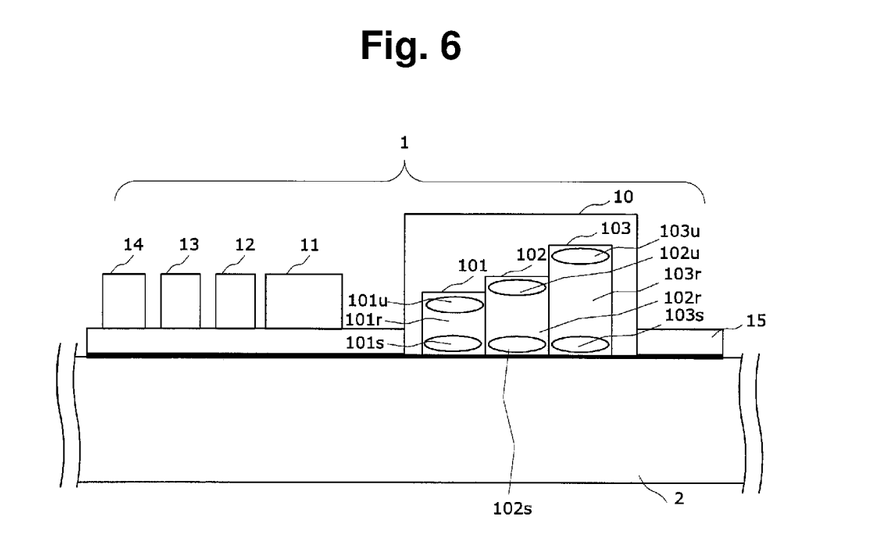
FIG. 6 is a block diagram showing a configuration of an in-vivo temperature measurement device according to an embodiment of the present invention.

The core temperature measurement instrument 10 includes three heat flux sensors 101, 102, and 103. The heat flux sensors 101, 102, and 103 are devices that measure heat transfer per unit time or per unit area.

The heat flux sensors 101, 102, and 103 include thermal resistors 101r, 102r, 103r, and temperature sensors (second temperature sensors) 101u, 102u, and 103u and temperature sensors (first temperature sensors) 101s, 102s, and 103s which are provided at both ends of the thermal resistors 101r, 102r, and 103r, respectively.

The thermal resistors 101r, 102r, and 103r provided in the heat flux sensors 101, 102, and 103, respectively, are made of heat insulating materials having different thickness and materials and have different thermal resistance values $R_{S1}$, $R_{S2}$, and $R_{S3}$, respectively.

The temperature sensors 101s, 102s, and 103s are provided on the thermal resistors 101r, 102r, and 103r to be closer to a living body 2, respectively, and measure the epidermis temperature $T_S$ (first temperature) of the living body 2.

The temperature sensors 101u, 102u, and 103u are provided on the thermal resistors 101r, 102r, and 103r to be opposite to the living body 2, respectively, and measure the upper surface temperature $T_U$ (second temperature) at a position away from the living body 2.

As the temperature sensors 101s to 103s and 101u to 103u, for example, a known thermistor or a thermopile using a thermocouple can be used.

The arithmetic circuit 11 includes a time count unit 11o and an estimation unit 11. The arithmetic circuit 11 estimates the core temperature $T_C(t)$ of the living body 2 based on the epidermis temperature $T_S(t)$ measured by the temperature sensors 101s to 103s and the upper surface temperature $T_U(t)$ measured by the temperature sensors 101u to 103u. More specifically, the estimation unit 111 estimates the core temperature $T_C$ by substituting the epidermis temperatures $T_{S1}$, $T_{S2}$, and $T_{S3}$ measured by the temperature sensors 101s to 103s and the upper surface temperatures $T_{U1}$, $T_{U2}$, and $T_{U3}$ measured by the temperature sensors 101u to 103u at a measurement time t of the time count unit 110 into Expression (5) representing the estimation model described above.

The arithmetic circuit 11 generates and outputs time-series data of the estimated core temperature $T_C$ of the living body 2. The time-series data is data in which the measurement time and the estimated core temperature $T_C$ are associated with each other.

The memory 12 stores information on the estimation model (Expression (5)) of the core temperature $T_C$ which is constructed in advance. In addition, the memory 12 also stores the thermal resistance values $R_{S1}$, $R_{S2}$, and $R_{S3}$ of the heat flux sensors 101, 102, and 103. The memory 12 can be realized by a predetermined storage region in a rewritable nonvolatile storage device (for example, a flash memory) provided in the in-vivo temperature measurement device 1.

The communication circuit 13 outputs the time-series data of the core temperature $T_C$ of the living body 2 generated by the arithmetic circuit 11 to the outside. Such a communication circuit 13 is an output circuit to which an USB or other cables can be connected when outputting data or the like in a wired manner, but, for example, a wireless communication circuit compliant with Bluetooth (registered trademark) may be used.

The sheet-shaped base 15 functions as a base on which the core temperature measurement instrument 10, the arithmetic circuit 11, the memory 12, the communication circuit 13, and the battery 14 are mounted, and also includes wirings through which these elements are electrically connected to each other. Considering that the in-vivo temperature measurement device 1 is connected onto the epidermis of the living body, a deformable flexible substrate is desirably used for the sheet-shaped base 15.

Further, an opening is provided in a part of the sheet-shaped base 15, and the heat flux sensors 101, 102, and 103 are mounted on the base 15 so as to contact with the epidermis of the living body 2 through the opening.

Here, the in-vivo temperature measurement device 1 is realized by a computer. Specifically, the arithmetic circuit 11 is realized in a manner that a processor such as a CPU or a DSP executes various data processing according to a program stored in a storage device including the memory 12 such as a ROM, a RAM, and a flash memory provided in the in-vivo temperature measurement device 1. The program for causing the computer to function as the in-vivo temperature measurement device 1 can be recorded in a recording medium or can also be provided through a network.

Operation of In-vivo Temperature Measurement Device

An operation of the in-vivo temperature measurement device 1 including the above-described configuration will be described below with reference to a flowchart of FIG. 8. The memory 12 stores, in advance, the estimation model (Expression (5)) of the core temperature $T_C$ and the thermal resistance values $R_{S1}$, $R_{S2}$, and $R_{S3}$ of the thermal resistors 101r, 102r, and 103r of the respective heat flux sensors 101, 102, and 103.

Further, the base 15 of the in-vivo temperature measurement device 1 is disposed in contact with the epidermis of the living body 2 in advance.

First, the arithmetic circuit 11 reads, from the memory 12, the estimation model (Expression (5)) of the core temperature $T_C$ and the thermal resistance values $R_{S1}$, $R_{S2}$, and $R_{S3}$ of the thermal resistors 101r, 102r, and 103r included in the respective heat flux sensors 101, 102, and 103 (step S1). The arithmetic circuit 11 sets the read thermal resistance values $R_{S1}$, $R_{S2}$, and $R_{S3}$ in the estimation model (Expression (5)).

Next, the temperature sensors 101s to 103s and 101u to 103u of the heat flux sensors 101, 102, and 103 measure the epidermis temperatures $T_{S1}$, $T_{S2}$, and $T_{S3}$ and the upper surface temperatures $T_{U1}$, $T_{U2}$, and $T_{U3}$ (step S2). The measured epidermis temperatures $T_{S1}$, $T_{S2}$, and $T_{S3}$ and the upper surface temperatures $T_{U1}$, $T_{U2}$, and $T_{U3}$ are sent to the arithmetic circuit 11.

Then, the estimation unit 11 substitutes the epidermis temperatures $T_{S1}$, $T_{S2}$, and $T_{S3}$ and the upper surface temperatures $T_{U1}$, $T_{U2}$, and $T_{U3}$ measured in step S2 into the estimation model of the above-described Expression (5) to estimate the core temperature $T_C$ (step S3). The estimated value of the core temperature $T_C$ of the living body 2 is stored in the memory 12.

Next, the arithmetic circuit 11 generates time-series data of the estimated core temperature $T_C$ (step S4). More specifically, the arithmetic circuit 11 repeatedly executes steps S2 and S3 to generate time-series data of the core temperature $T_C$. The generated time-series data of the core temperature $T_C$ is stored in the memory 12.

Then, the arithmetic circuit 11 outputs the generated time-series data of the core temperature $T_C$ to the outside through the communication circuit 13 (step S5). For example, the time-series data of the core temperature $T_C$ is displayed on a display screen of a smartphone or a tablet terminal via a communication network (not shown).

Measurement Result of In-Vivo Temperature Measurement Device

A result of the core temperature $T_C$ measured by the in-vivo temperature measurement device 1 according to the present embodiment will be described below with reference to FIGS. 9A and 9B.

Figure 9A:
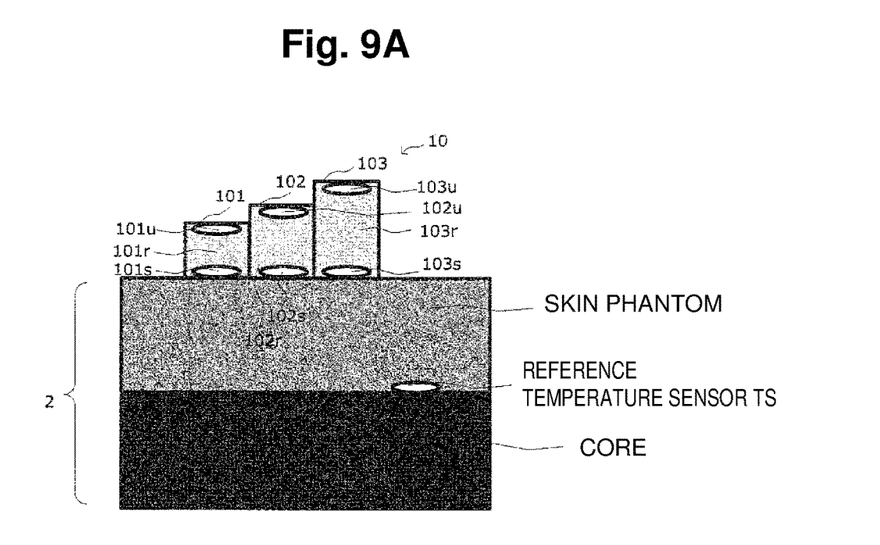
FIG. 9A is a diagram for explaining measurement of a core temperature with the in-vivo temperature measurement device according to the embodiment of the present invention.

As shown in FIG. 9A, in the measurement of the core temperature $T_C$ by the in-vivo temperature measurement device 1, a reference temperature sensor $T_S$ for measuring a reference temperature of the core as a heat source is used for comparison. Further, according to the conventional example for comparison, the core temperature $T_C$ is measured based on the estimation model (for example, FIGS. 2 and 3) in which only a thermal equilibrium state is defined.

Both the in-vivo temperature measurement device 1 of the present embodiment and the in-vivo temperature measurement device of the conventional example are installed on the surface of the skin phantom under the same conditions and measure the temperature. In FIG. 9A, only the core temperature measurement instrument 10 of the in-vivo temperature measurement device 1 is schematically shown.

Figure 9B:
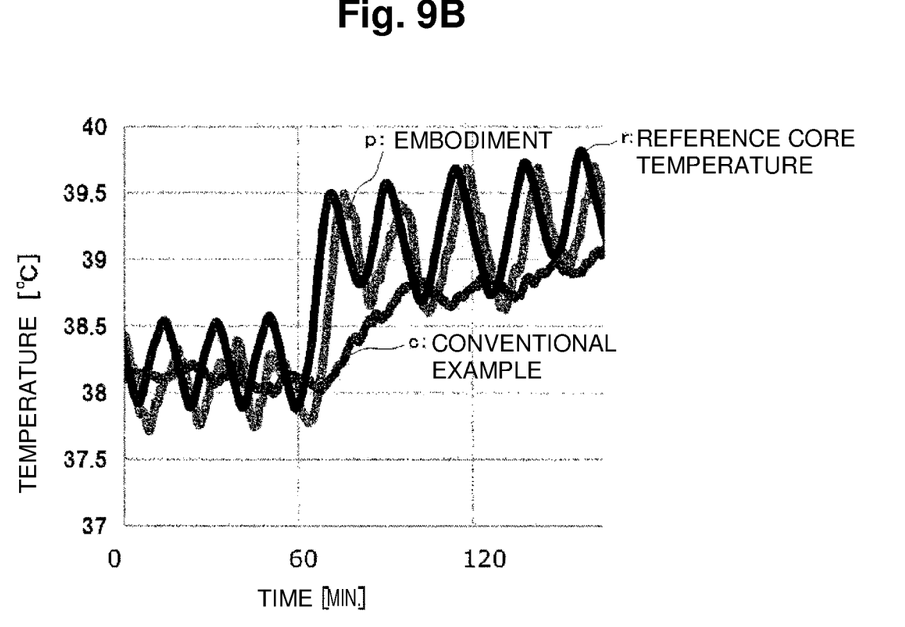
FIG. 9B is a diagram illustrating a result measured by the in-vivo temperature measurement device according to the embodiment of the present invention.

FIG. 9B shows measurement results. In FIG. 9B, a horizontal axis represents a measurement time (minute), and a vertical axis represents a core temperature $T_C$ (° C.). As can be seen from FIG. 9B, a measurement result "c" according to the conventional example has a large error with respect to a reference core temperature "r". On the other hand, it can be seen that a measurement result "p" by the in-vivo temperature measurement device 1 of the present embodiment has a small error with respect to the reference core temperature "r".

As described above, the in-vivo temperature measurement device 1 according to the present embodiment uses the estimation model in consideration with the non-thermal equilibrium state in the living body 2 to estimate the core temperature $T_C$ using the epidermis temperatures $T_{S1}$, $T_{S2}$, and $T_{S3}$ and the upper surface temperatures $T_{U1}$, $T_{U2}$, and $T_{U3}$ measured by the temperature sensors 101s to 103s and 101u to 103u. Therefore, it is possible to improve the measurement accuracy compared with the core temperature $T_C$ estimated by the conventional estimation model in which only the thermal equilibrium state is defined, and to more accurately estimate the core temperature that changes every moment.

As a result, it is possible to evaluate physical and mental disorders due to social jet-lag, for example, to grasp the consistency or inconsistency between the time of sleep or wake-up and the biological rhythm of an individual.

In the embodiment described above, a case has been described in which the core temperature measurement instrument 10 and the arithmetic circuit 11 are configured in the same casing, but the arithmetic circuit 11 may be configured independently of the core temperature measurement instrument 10. For example, the arithmetic circuit 11 may be configured to transmit the respective temperatures measured by the core temperature measurement instrument 10 to terminals, for example, a server device, PC, and a smartphone, through a communication network, and to perform an arithmetic process.

Although the embodiment of the in-vivo temperature measurement device and the in-vivo temperature measurement method of embodiments of the present invention has been described above, the present invention is not limited to the embodiment described above, and various modifications that can be envisioned by those skilled in the art can be made within the scope of the invention described in the claims.

REFERENCE SIGNS LIST

1 In-vivo temperature measurement device
2 Living body
10 Core temperature measurement instrument
11 Arithmetic circuit
12 Memory
13 Communication circuit
14 Battery
15 Base
101, 102, 103 Heat flux sensor
101u, 102u, 103u, 101s, 102s, 103s Temperature sensor 110 Time count unit
111 Estimation unit.

The invention claimed is:

1. An in-vivo temperature measurement device comprising:
   a plurality of thermal resistors;
   a plurality of first temperature sensors at a first end of the plurality of thermal resistors configured to face a living body;
   a plurality of second temperature sensors provided at a second end of the plurality of thermal resistors opposite to the first end;
   a memory configured to store an estimation model of a core temperature of the living body according to a non-thermal equilibrium state of the living body and thermal resistance values of the plurality of thermal resistors; and
   an arithmetic circuit configured to estimate the core temperature of the living body based on the estimation model, the thermal resistance values, and a plurality of temperatures measured by the plurality of first temperature sensors and the plurality of second temperature sensors;
   wherein the first temperature sensors are configured to measure a first temperature indicating an epidermis temperature of the living body;
   wherein the second temperature sensors are configured to measure a second temperature at a position away from the living body;
   wherein the thermal resistance values of the plurality of thermal resistors are different from one another; and
   wherein the estimation model is represented by a following expression:

$$T_C = \frac{T_1(T'_{S2}T_{S3} - T'_{S3}T_{S2}) + \frac{R_{S1}}{R_{S2}}T_2(T'_{S3}T_{S1} - T'_{S1}T_{S3}) + \frac{R_{S1}}{R_{S3}}T_3(T'_{S1}T_{S2} - T'_{S2}T_{S1})}{T_1(T'_{S2} - T'_{S3}) + \frac{R_{S1}}{R_{S2}}T_2(T'_{S3} - T'_{S1}) + \frac{R_{S1}}{R_{S3}}T_3(T'_{S1} - T'_{S2})},$$

wherein $T_c$ indicates the core temperature at a measurement time t, $R_{Si}$ (i=1, 2, 3) indicates a corresponding thermal resistance value of each of the plurality of thermal resistors, $T_{Si}$ (i=1, 2, 3) indicates a corresponding first temperature measured by each of the plurality of first temperature sensors, $T_i$, =($T_{Si}$(t)-$T_{Ui}$(t)), $T_{Ui}$ (i=1, 2, 3) indicates a corresponding second temperature measured by each of the plurality of second temperature sensors, and $T_{Si}' = dT_{Si}(t)/dt$.

2. The in-vivo temperature measurement device according to claim 1, wherein
   the arithmetic circuit includes:
      a time counter configured to count measurement times at which the plurality of first temperature sensors and the plurality of second temperature sensors measure the plurality of temperatures; and
      an estimation circuit configured to, based on the plurality of temperatures measured by the first temperature sensors and the second temperature sensors at the measurement times, estimate the core temperature of the living body using the estimation model and the thermal resistance values of the thermal resistors; and wherein the arithmetic circuit is configured to generate time-series data associating the measurement times and the core temperature.

3. The in-vivo temperature measurement device according to claim 1, wherein
the plurality of thermal resistors comprise three thermal resistors.

4. The in-vivo temperature measurement device according to claim 1, further comprising a communication circuit configured to transmit the core temperature estimated by the arithmetic circuit.

5. The in-vivo temperature measurement device according to claim 1, wherein thicknesses of the plurality of thermal resistors are different from one another.

6. An in-vivo temperature measurement method comprising:
measuring a plurality of temperatures with first temperature sensors and second temperature sensors, wherein the first temperature sensors are provided at a first end of a plurality of thermal resistors, wherein the second temperature sensors are provided at a second end of the plurality of thermal resistors opposite to the first end, and wherein the first temperature sensors are positioned facing a living body; and
estimating, using an estimation model of a core temperature based on a non-thermal equilibrium state of the living body and thermal resistance values of the thermal resistors, the core temperature of the living body based on the plurality of temperatures;
wherein the first temperature sensors measure a first temperature indicating an epidermis temperature of the living body;
wherein the second temperature sensors measure a second temperature at a position away from the living body;
wherein the thermal resistance values of the plurality of thermal resistors are different from one another; and wherein the estimation model is represented by a following expression:

$$T_C = \frac{T_1(T'_{S2}T_{S3} - T'_{S3}T_{S2}) + \frac{R_{S1}}{R_{S2}}T_2(T'_{S3}T_{S1} - T'_{S1}T_{S3}) + \frac{R_{S1}}{R_{S3}}T_3(T'_{S1}T_{S2} - T'_{S2}T_{S1})}{T_1(T'_{S2} - T'_{S3}) + \frac{R_{S1}}{R_{S2}}T_2(T'_{S3} - T'_{S1}) + \frac{R_{S1}}{R_{S3}}T_3(T'_{S1} - T'_{S2})},$$

wherein $T_c$ indicates the core temperature at a measurement time t, $R_{Si}$ (i=1, 2, 3) indicates a corresponding thermal resistance value of each of the plurality of thermal resistors, $T_{Si}$ (i=1, 2, 3) indicates a corresponding first temperature measured by each of the first temperature sensors, $T_i$, =($T_{Si}$(t)-$T_{Ui}$(t)), $T_{Ui}$ (i=1, 2, 3) indicates a corresponding second temperature measured by each of the second temperature sensors, and $T_{Si}' = dT_{Si}(t)/dt$.

7. The method according to claim 6, wherein estimating the core temperature of the living body comprises:
counting measurement times at which the first temperature sensors and the second temperature sensors measure the plurality of temperatures; and
based on the plurality of temperatures measured by the first temperature sensors and the second temperature sensors at the measurement times, estimating the core temperature of the living body using the estimation model and the thermal resistance values of the thermal resistors; and
generating time-series data associating the measurement times and the core temperature.

8. The method according to claim 6, wherein the plurality of thermal resistors comprise three thermal resistors.

9. The method according to claim 6, further comprising reading the thermal resistance values from the plurality of thermal resistors.

10. The method according to claim 6, wherein the second temperature sensors measure the second temperature at an upper surface of the plurality of thermal resistors.

* * * * *